June 3, 1941. W. W. SMITH, JR Plant Pat. 470
SANSEVIERIA
Filed July 18, 1940
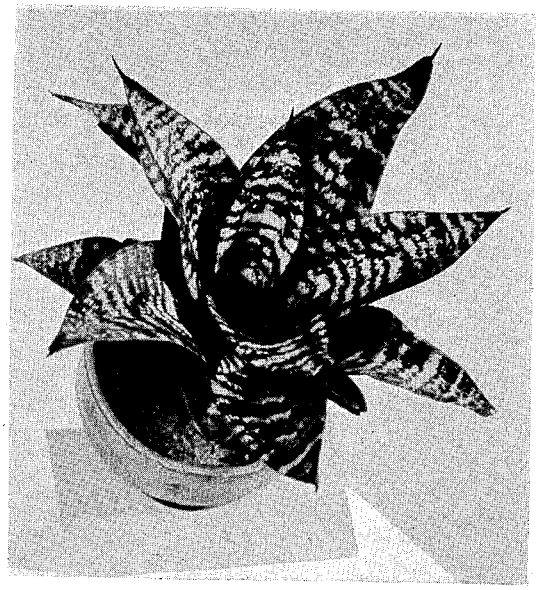
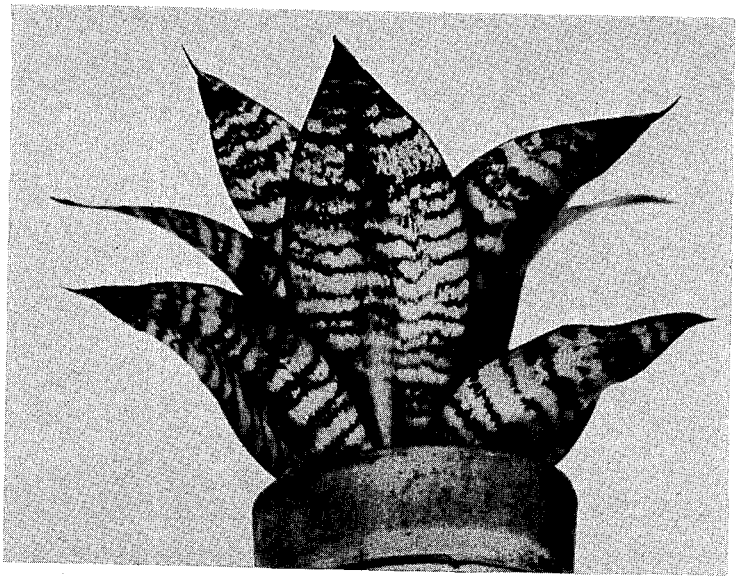
INVENTOR
William Walter Smith Jr
By Orville M. Kile
Plant Patent Agent Patented June 3, 1941

Plant Pat. 470

UNITED STATES PATENT OFFICE

470

SANSEVIERIA

William Walter Smith, Jr., New Orleans, La., assignor, by mesne assignments, to Sylvan Hahn, Pittsburgh, Pa.

Application July 18, 1940, Serial No. 346,220

1 Claim. (Cl. 47—59)

My present invention relates to an improved variety of Sansevieria plant, the principal claim to novelty residing in its compact spiral growth. Whereas other known Sansevieria varieties grow erect from the base, with tips slightly spreading, this variety grows with the leaves tiering up one after the other in a definite spiral and with the tips widely spreading.

The new variety is a sport of the variety Laurenti and was discovered by me on the property of my father, William W. Smith, owner and proprietor of the Crescent Nursery Company of New Orleans, Louisiana.

The variety has been asexually reproduced both by suckers and by leaf cuttings and its characteristics have always reproduced true in both types of reproduction. This variety differs from its parent in the matter of reproducing true from leaf cuttings, inasmuch as the parent variety comes entirely green rather than with a golden edge, if leaf cuttings are used. No leaf cuttings of any other variety of Sansevieria have ever produced any of the rosette type of plant, so far as I am able to learn. Occasionally some of the older varieties have produced rosettes from sucker cuttings. However even these do not remain true rosette types but grow into the taller types. Every specimen of the new variety has remained the true rosette type, reproducing true either from suckers or from leaf cuttings.

The shape of the leaves of this new variety is quite different from that of other known varieties, the present one being much broader. The present variety may be described as having a narrow-ovate leaf with tips drawn to very short points and arising from a narrow thin base, while other varieties have leaves that are lanceolate to linear with tips drawn to long sharp points and arising from a narrow thick base.

The illustrations accompanying the application show two views of three-year plants of this new variety, one plant as though viewed from the side and the other as though viewed from the top. Both views indicate the short, broad leaves, and the view from the top indicates the spiral growth.

Following is a description of this new variety in greater detail:

Growth:

*Type.*—Compact, flat spiral or rosette; base of plant narrow and thin.

*Rapidity.*—Grows and reproduces rapidly and with ease.

*Size.*—Original plant has attained a size of 18 inches in height after several years' growth.

Leaves:

*Shape.*—Much broader and shorter than other known varieties. Norrow-ovate; very short point on older leaves. Young leaves concave; older leaves flat.

*Size.*—Average size 12 centimeters long by 6 centimeters broad through center.

*Margin.*—Entire; somewhat undulating.

*Color.*—Metallic colored transverse bands about 7 millimeters broad alternate with broader green bands. These bands, however, are not definitely delineated. General color is approximately the same as that of the variety Zeylonica.

*Position.*—Spreading from base; upper third horizontal to slightly reflexed.

*Base.*—Narrow.

Flowers: No flowers or fruit have ever been observed, although when the plants grow much older they may have such characters.

Having thus disclosed my discovery, I claim:

A new and distinct variety of Sansevieria plant substantially as shown and described, characterized particularly by its definitely flat spiral growth; its broad, short-pointed leaves with alternating metallic and green indefinite bands; and its ability to reproduce true by leaf cuttings as well as by suckers.

WILLIAM WALTER SMITH, Jr.